United States Patent
Kagarise

(10) Patent No.: US 8,097,012 B2
(45) Date of Patent: Jan. 17, 2012

(54) ENDOCARDIAL LEAD REMOVING APPARATUS

(75) Inventor: Brian Kagarise, Colorado Springs, CO (US)

(73) Assignee: The Spectranetics Corporation, Colorado Springs, CO (US)

( * ) Notice: Subject to any disclaimer, the term of this patent is extended or adjusted under 35 U.S.C. 154(b) by 144 days.

(21) Appl. No.: 11/190,550

(22) Filed: Jul. 27, 2005

(65) Prior Publication Data
US 2011/0208207 A1 Aug. 25, 2011

(51) Int. Cl.
*A61B 17/32* (2006.01)
(52) U.S. Cl. .................... 606/170; 606/167; 606/171
(58) Field of Classification Search .............. 606/167, 606/170, 171, 148, 144
See application file for complete search history.

(56) References Cited

U.S. PATENT DOCUMENTS

| | | | |
|---|---|---|---|
| 4,559,041 A | 12/1985 | Razi | |
| 5,171,314 A | 12/1992 | Dulebohn | |
| 5,474,532 A * | 12/1995 | Steppe | 604/22 |
| 5,591,187 A | 1/1997 | Dekel | |
| 5,665,062 A | 9/1997 | Houser | |
| 5,709,697 A | 1/1998 | Ratcliff et al. | |
| 5,766,177 A | 6/1998 | Lucas-Dean et al. | |
| 5,779,715 A | 7/1998 | Tu | |
| 5,863,294 A * | 1/1999 | Alden | 606/167 |
| 5,868,768 A | 2/1999 | Wicherski et al. | |
| 5,873,886 A | 2/1999 | Larsen et al. | |
| 5,913,867 A | 6/1999 | Dion | |
| 6,004,335 A | 12/1999 | Vaitekunas et al. | |
| 6,033,402 A | 3/2000 | Tu et al. | |
| 6,110,177 A | 8/2000 | Ebner et al. | |
| 6,139,508 A | 10/2000 | Simpson et al. | |
| 6,142,997 A | 11/2000 | Michelson | |
| 6,241,692 B1 | 6/2001 | Tu et al. | |
| 6,267,732 B1 | 7/2001 | Heneveld et al. | |
| 6,383,145 B1 | 5/2002 | Worm et al. | |
| 6,419,684 B1 * | 7/2002 | Heisler et al. | 606/170 |

(Continued)

FOREIGN PATENT DOCUMENTS

| | | |
|---|---|---|
| WO | WO 03/022157 | 3/2003 |
| WO | WO 2004/073524 | 9/2004 |

OTHER PUBLICATIONS

International Search Report for International (PCT) Patent Application No. PCT/US06/28960, mailed Apr. 9, 2007, 1 page.

(Continued)

*Primary Examiner* — Corrine M McDermott
*Assistant Examiner* — Melissa Ryckman
(74) *Attorney, Agent, or Firm* — Scott J. Hawranek; Sheridan Ross, P.C.

(57) ABSTRACT

The invention provides an apparatus having a tubular member for receiving an endocardial lead implanted within a patient's body. Disposed generally at a distal end of the tubular member is at least one blade or cutting surface. An adjustment mechanism moves the blade between retracted and extended positions to engage the cutting surface with the endocardial lead to cut the lead. Once severed, the cut portion of the lead remains within an inner channel of the tubular member and the apparatus and cut portion of the lead are removed from within the patient. Various embodiments include the blade pivotally connected to the distal end of the tubular member and activated by a wire adjustment mechanism. Others include a metallic wire for slicing through the lead. Still others include a pneumatically actuated adjustment mechanism that inflates to move the blade and engage the cutting surface with the lead.

11 Claims, 8 Drawing Sheets

U.S. PATENT DOCUMENTS

| | | | |
|---|---|---|---|
| 6,432,115 B1 * | 8/2002 | Mollenauer et al. | 606/148 |
| 6,443,966 B1 | 9/2002 | Shiu | |
| 6,447,525 B2 | 9/2002 | Follmer et al. | |
| 7,993,359 B1 | 8/2011 | Atwell et al. | |
| 2002/0177843 A1 | 11/2002 | Anderson et al. | |
| 2003/0078609 A1 | 4/2003 | Finlay et al. | |

OTHER PUBLICATIONS

International Preliminary Report on Patentability for International (PCT) Patent Application No. PCT/US06/28960, issued Jan. 29, 2008, 6 pages.

* cited by examiner

ENDOCARDIAL LEAD REMOVING APPARATUS

FIELD OF THE INVENTION

This invention relates generally to an endocardial lead removing apparatus and, more particularly, to an apparatus that cuts the endocardial lead and, in some embodiments, captures the cut portion to remove the lead from the patient's body.

BACKGROUND OF THE INVENTION

In the past, various types of endocardial leads and electrodes have been introduced into different chambers of a patient's heart, including among other locations, the right ventricle, right atrial appendage, and atrium, as well as the coronary sinus. These flexible leads are often composed of an insulator sleeve that contains an implanted helical coil conductor that is attached to an electrode tip. This electrode is placed in contact with myocardial tissue by passage through a venous access, often the subclavian vein or one of its tributaries, which leads to the endocardial surface of the heart chambers. The tip with the electrode contact is held in place by trabeculations of myocardial tissue. In some cases, active fixation leads are fastened by screw into the myocardial tissue.

The tips of many available leads often include flexible tines, wedges, or finger-like projections which extend radially outward and usually are molded from and integral with the insulating sheath of the lead. These tines or protrusions allow surrounding growth of tissue in chronically implanted leads to fix the electrode tip in position in the heart and prevent dislodgement of the tip during the life of the lead. In "acute placement" of the electrode or lead tip, a blood clot forms about the flanges or tines (due to enzymes released as a result of irritation of the trabeculations of myocardial tissue by the presence of the electrode tip) until scar tissue eventually forms, usually in three to six months. The tines or wedges or finger-like projections allow better containment by the myocardial trabeculations of muscle tissue and prevent early dislodgement of the lead tip.

Although the state of the art in implemented pulse generator or pacemaker technology and endocardial lead technology has advanced considerably, endocardial leads nevertheless occasionally fail, due to a variety of reasons, including breakage of a lead, insulation breaks, breakage of the inner helical coil conductor and an increase in electrode resistance. Furthermore, in some instances, it may be desirable to electronically stimulate different portions of the heart than are presently being stimulated with the leads already implanted. There are a considerable number of patients who have one or more, and sometimes as many as four or five, unused leads in their veins and heart.

Although it obviously would be desirable to easily remove such unused leads, in the past surgeons usually have avoided attempts to remove inoperative leads because the risk of removing them exceeded the risk of leaving them in. The risks of leaving unused myocardial leads in the heart and venous path include increased likelihood that an old lead may facilitate infection, which in turn may necessitate removal of the lead to prevent continued bacteremia and abcess formation. Furthermore, there is an increased likelihood of the formation of blood clots in the atrial chamber about entangled leads. Such clots may embolize to the lung and produce severe complications and even fatality. Furthermore, the presence of unused leads in the venous pathway and inside the heart can cause considerable difficulty in the positioning and attachment of new endocardial leads in or to the heart.

Removal of an inoperative lead sometimes can be accomplished by applying traction and rotation to the outer free end of the lead, but only if done prior to fixation of the lead tip in the trabeculations of myocardial tissue by scar tissue formation or large clot development. Even then, it is possible that a clot has formed so the removal of the leads causes various sized emboli to pass to the lungs, producing severe complications.

In cases where the lead tip has become attached by scar tissue to the myocardial wall, removal of the lead always has presented problems and risks. Porous lead tips that are sometimes used may have an in-growth of scar tissue attaching them to the myocardial wall. Sufficient traction on such leads in a removal attempt could cause disruption of the myocardial wall prior to release of the embedded lead tip. The tines or flanges of other types of leads that are not tightly scarred to the myocardial wall present similar risks. Even if screw-in tip electrodes are used, wherein the tips theoretically can be unscrewed from the myocardial wall, unscrewing of such tips may be prevented by a channel of scar tissue and endothelium that surrounds the outer surface of the lead along the venous pathway. Such "channel scar" tissue prevents withdrawal because of tight encasement of the lead. Continual strong pulling or twisting of the outer free end of the lead could cause rupture of the atrial wall or the ventricular wall if there is such tight circumferential encasement of adherent channel scar tissue in the venous path. Such tight encasement by scar tissue in the venous pathway and in the trabeculations of the myocardial wall typically occurs within six months to a year of the initial placement of the lead.

The risks of removing the lead by such traction and rotation of the lead may be high enough so that, if it becomes imperative that the lead be removed (as in the case of infection), many surgeons have elected to open the patient's chest and surgically remove the lead rather than attempt removal by applying traction and rotation thereto.

Clearly, there is a need for an apparatus for extracting endocardial leads from a patient's body with minimized risk to the patient.

SUMMARY OF THE INVENTION

To address these and other drawbacks in the existing art, the present invention comprises an apparatus for grasping a free end of an endocardial lead and cutting the lead as near as possible to the lead's embedded electrode. Once the lead is severed, a majority of the lead is removed thereby, leaving just a small distal portion of the lead within the patient.

Specifically, the present invention comprises an apparatus having a tubular member for receiving the lead. Positioned generally at a distal end of the tubular member is at least one blade or cutting surface. In some embodiments, an adjustment mechanism actuates the blade between extended and retracted positions to engage the cutting surface with the lead to cut the lead. Once severed, the cut portion of the lead is disposed within the tubular member and the apparatus is removed from within the patient.

Other aspects of the invention will be apparent to those skilled in the art after reviewing the drawings and the detailed description below.

BRIEF DESCRIPTION OF THE DRAWINGS

The present invention will now be described, by way of example, with reference to the accompanying drawings, in which.

DETAILED DESCRIPTION

Referring generally to FIGS. 1-12, various embodiments of an endocardial lead removing apparatus are generally referred to at 10.

Figure 1:
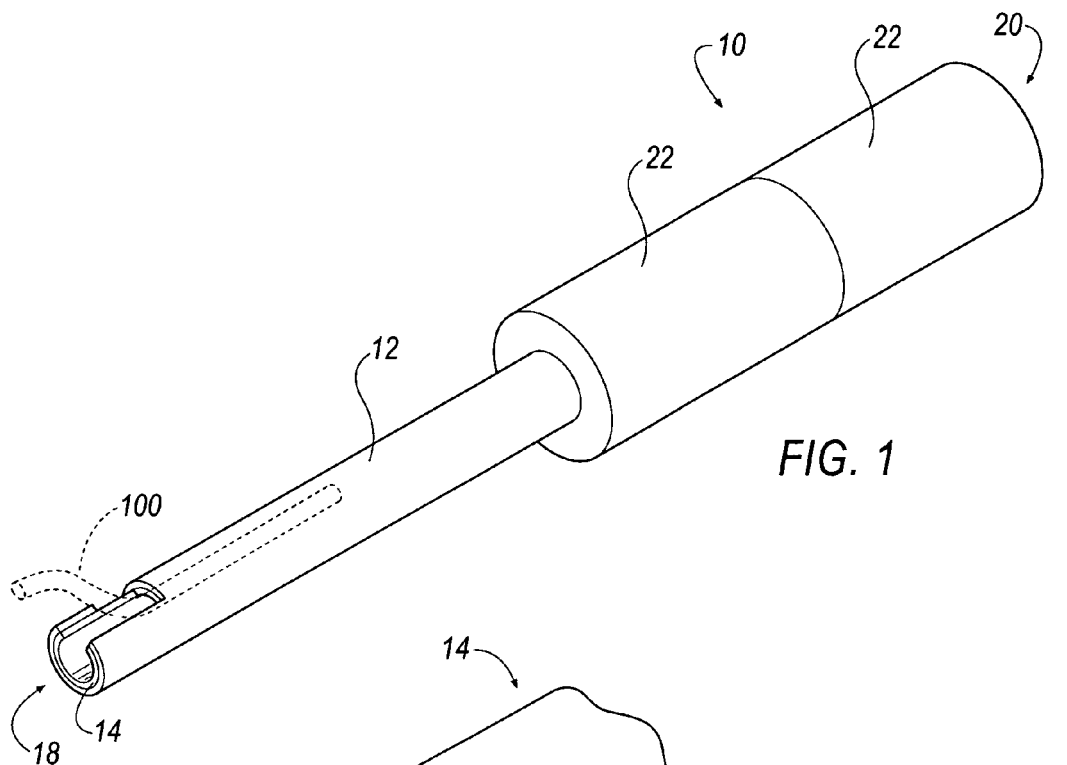
FIG. 1 illustrates a perspective view of an endocardial lead removing apparatus of a first embodiment of the present invention.
Figure 2A:
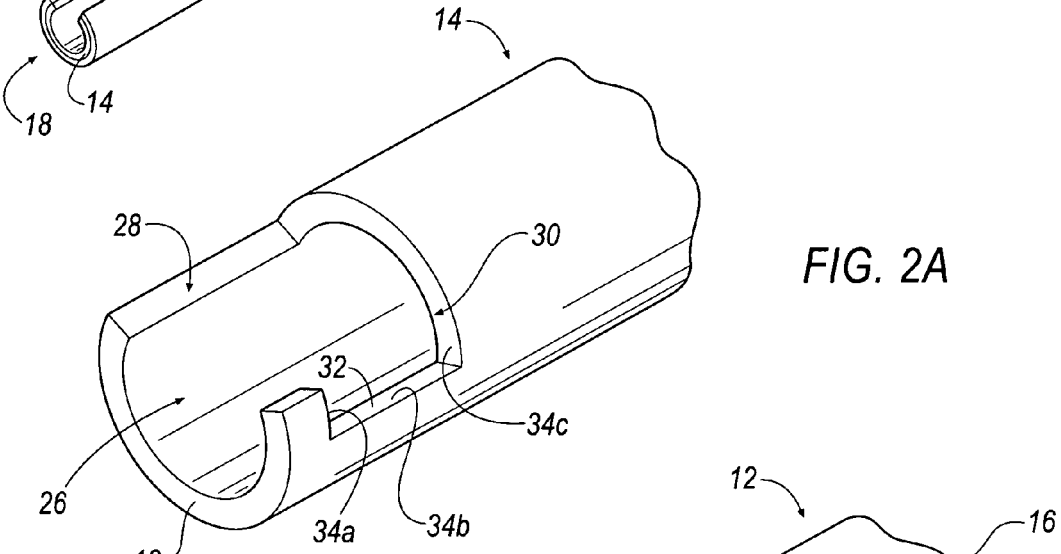
FIG. 2A illustrates a perspective view of a distal end of an inner tubular member of the first embodiment of the present invention.
Figure 2B:
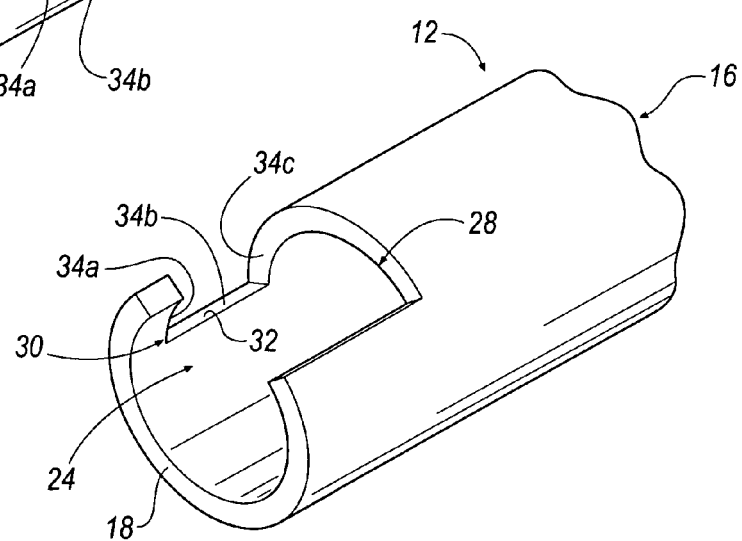
FIG. 2B illustrates a perspective view of a distal end of an outer tubular member of the first embodiment of the present invention.

Referring to FIG. 1, in some embodiments, the invention comprises an apparatus 10 that includes an outer tubular member 12 and an inner tubular member 14. Each tubular member 12, 14 includes an inner cavity 16. The inner tubular member 14 is received within the inner cavity 16 of the outer tubular member 12. Both of the members 12, 14 have distal ends 18 and proximal ends 20 with the proximal ends 20 of each member 12, 14 having a handle 22. As shown, the outer tubular member 12 has a generally shorter length than the inner tubular member 14 and the handles 22 generally abut at the proximal ends 20. Further, the members 12, 14 are contemplated to be made of a metallic material such as hardened stainless steel; however other materials, such as rigid plastic, are also contemplated by the present invention.

Generally disposed at the distal ends 18 of the outer member 12 and the inner member 14 are first and second channels 24, 26, respectively. As shown in FIGS. 2A-2B and 3A-3B, without limitation, the channels 24, 26 are generally L-shaped each having a longitudinal leg 28 and a lateral leg 30. The lateral legs 30 of each channel 24, 26 are generally orthogonal to the longitudinal legs 28. When assembled and having the inner tubular member 14 received in the inner cavity 16 of the outer tubular member 12, the first and second channels 24, 26 are opposed. As such, the lateral legs 30 of each channel 24, 26 align and extend orthogonally from the longitudinal legs 28 in opposite directions. Further, each of the channels 24, 26 includes at least one cutting surface 32. In some embodiments, without limitation, the invention may also comprise an inner tubular member 14 disposed in an outer tubular member 12 each with a T-shaped channel that forms a double blade with one or more cutting surfaces 32 on each member (FIG. 3C).

Figure 3A:
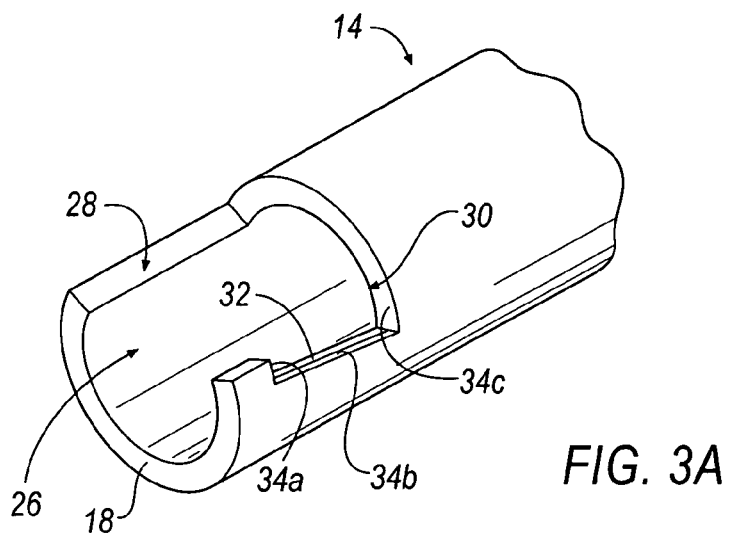
FIG. 3A illustrates a perspective view of the distal end of the inner tubular member of the first embodiment of the present invention having an angled cutting surface.
Figure 3B:
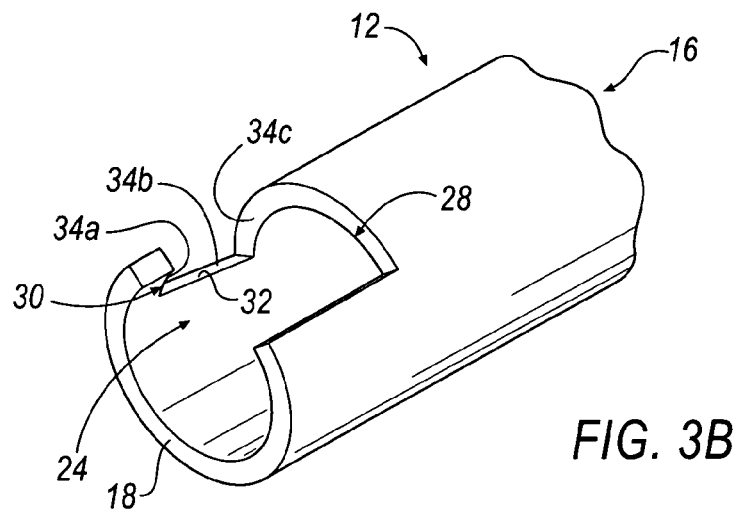
FIG. 3B illustrates a perspective view of the distal end of the outer tubular member of the first embodiment of the present invention having an angled cutting surface.
Figure 3C:
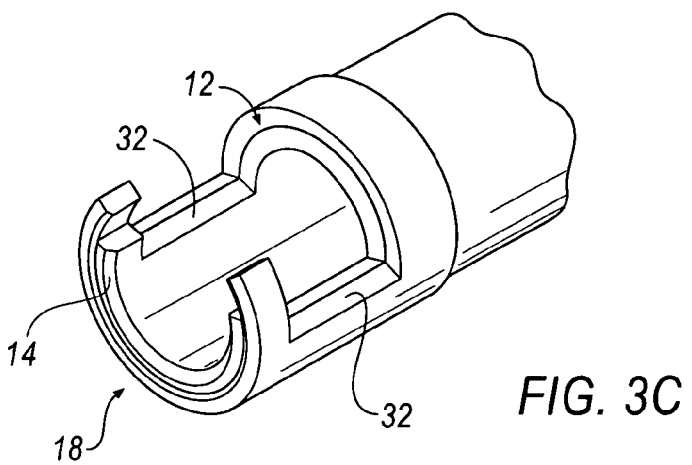
FIG. 3C illustrates a first embodiment of the present invention having a T-shaped cutting channel.

Referring to FIGS. 2A-2B and 3A-3B, the distal ends 18 of the inner and outer tubular members 12, 14 are illustrated. The channels 24, 26 are bounded by a plurality of edges 34. Specifically, the lateral legs 30 of each channel 24, 26 are bounded by three edges 34a, 34b and 34c. At least one of the three edges 34a-c is the cutting surface 32 described above. As contemplated for the illustrated embodiment, the cutting surface 32 is edge 34b. Alternatively, the present embodiment could include multiple cutting surfaces 32 such as each of the three edges 34a-c. Referring to FIGS. 3A-3B, the edge 34b may be generally angled to improve cutting efficiency of the apparatus 10.

Figure 1A:
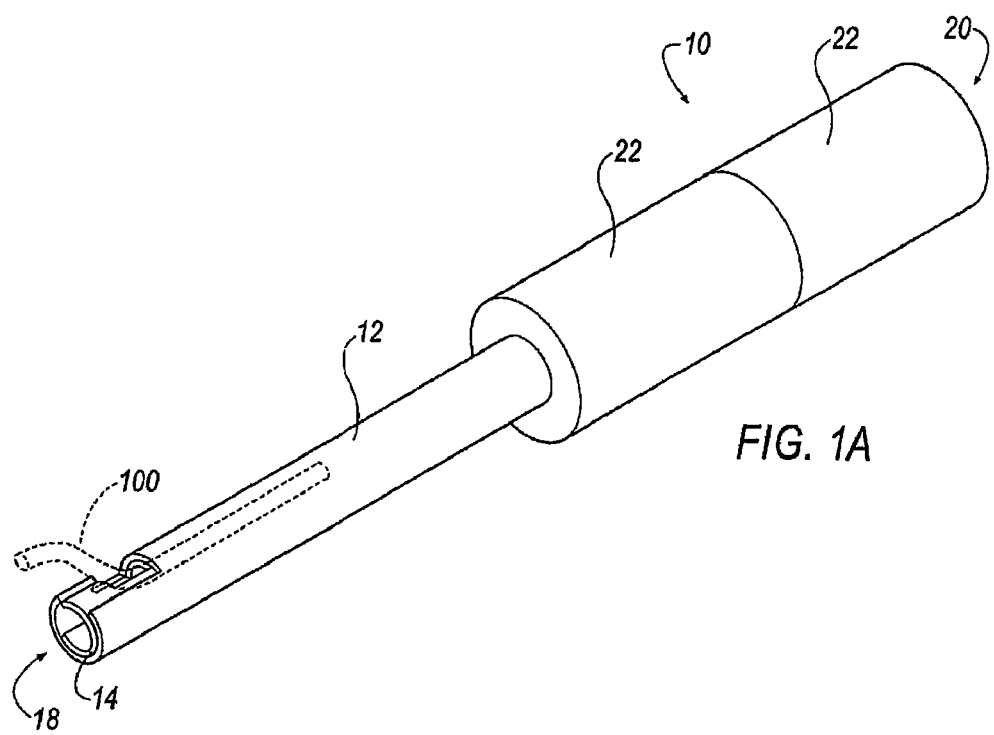
FIG. 1A illustrates the endocardial lead removing apparatus of FIG. 1 showing a window formed when inner and outer members are rotated relative to each other.

In operation, the first embodiment of apparatus 10 of FIGS. 1-3 is inserted within a patient's chest cavity, blood vessel, or other anatomical part containing a lead (not shown) and receives a lead 100 (shown in phantom in FIG. 1) within the inner cavity 16 of the inner tubular member 14. Once the distal ends 18 of the apparatus 10 are positioned as near as possible to the embedded electrode (not shown) within the patient's body the lead 100 is received within the channels 24, 26. Each of the tubular members 12, 14 are independently rotatable and when rotated in opposite directions the lead 100 is captured in a completely enclosed window formed between the cutting surfaces 32 of each channel 24, 26 as shown in FIG. 1A. Additional torque applied to the handles 22 and further rotation of the members 12, 14 cuts through the lead 100. The severed portion of the lead 100 remains within the inner cavity 16 of the inner tubular member 14 and the apparatus 10 is removed from the patient's body.

Figure 4:
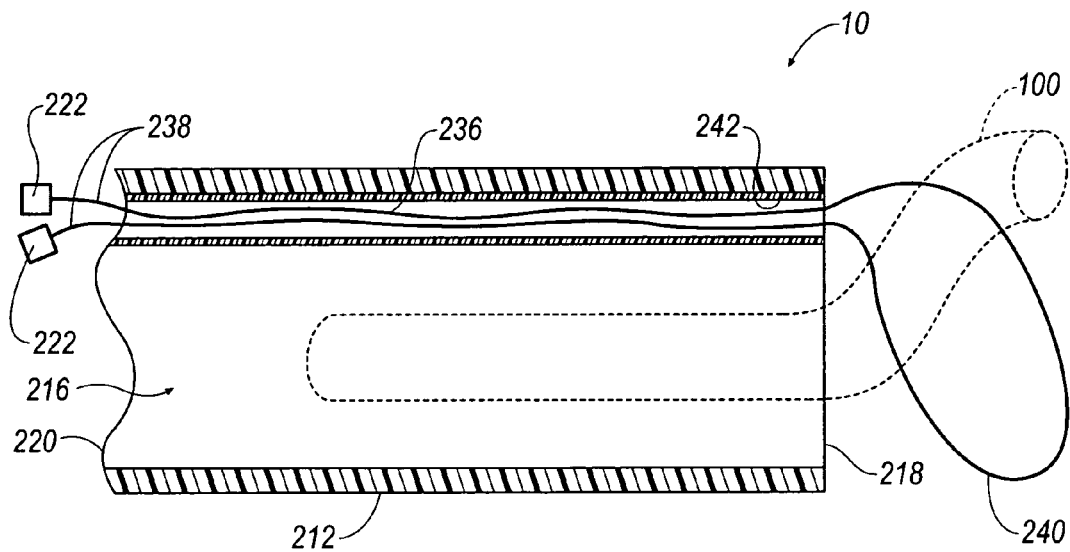
FIG. 4 illustrates a cross-sectional view along a longitudinal axis of a tubular member of an endocardial lead removing apparatus of another embodiment of the present invention.
Figure 5:
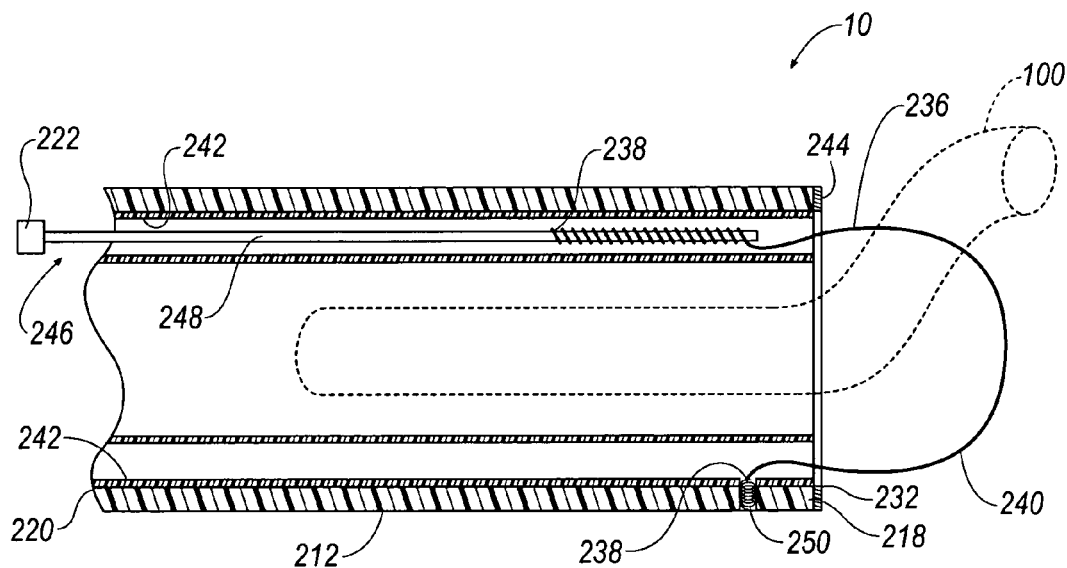
FIG. 5 illustrates a perspective view of the endocardial lead removing apparatus of an embodiment including an insert and adjustment mechanism.

Another embodiment of the apparatus 10 is shown in FIGS. 4-5. The embodiment includes a tubular member 212 having a distal end 218 and a proximal end 220. The tubular member 212 is generally flexible and made from a polymer material. Further, the tubular member 212 may include reinforcements such as a braid or compressed coil (not shown) to strengthen the tubular member 212 and resist compression during operation.

Disposed within an inner cavity 216 of the tubular member 212 is a metallic wire 236. In some embodiments, without limitation, a filament or strong cord, optionally diamond-coated, or other element suitable for cutting, may be substituted for the metallic wire. The metallic wire 236 has opposite ends 238 extending from the proximal end 220 of the tubular member 212. Optionally, the opposite ends 238 of the metallic wire 236 include handles 222. The metallic wire 236 extends through the inner cavity 216 and outwardly at the distal end 218 thereby forming a loop 240. It is contemplated that the metallic wire 236 is made from stainless steel or nickel titanium and has a diameter of about 0.005 inches to about 0.030 inches; however, other materials and diameters are also contemplated by the present invention.

Also disposed within the inner cavity 216 of the tubular member 212 is at least one lumen 242 for receiving the metallic wire 236. The lumen could be a second polymer lumen, even include a lubricious sleeve (such as polytetrafluoroethelene (PTFE) or FEP). The lumen 242 may be made from a flexible material such as nickel titanium, although other materials are also contemplated. The lumen 242 is disposed at one side of the inner cavity 216. The lumen 242 extends the length of the tubular member 212 and when only one lumen 242 is contemplated the opposite ends 238 of the metallic wire 236 are both disposed therein. Alternatively, two lumen 242, one for each opposite end 238 of the metallic wire 236, may be positioned adjacent to each other at one side of the inner cavity 216 of the tubular member 212.

In some embodiments, the invention also comprises an adjustment mechanism 246 (FIG. 5). The adjustment mechanism 246 moves the opposite ends 238 of the metallic wire 236 to reduce or expand the size of the loop 240. As shown, the adjustment mechanism 246 includes a rotatable pin 248 disposed within the inner cavity 216 at one side, optionally within a catheter 242. One of the opposite ends 238 of the metallic wire 236 is fixed to the rotatable pin 248. The second of the opposite ends 238 is fixed to a tension mechanism 250 such as a spring and the like. A handle 222 is disposed at a proximal end 220 to rotate the rotatable pin 248 and wind the metallic wire 236 thereabout.

In operation, the apparatus 10 of FIG. 4 includes the metallic wire 236 extending at the distal end 218 of the tubular member 212 to form the loop 240. The apparatus 10 is inserted within a patient and positioned near the lead 100. The free end of the lead 100 is received within the inner cavity 216 of the tubular member 212 and extends outwardly at the distal end 218 and through the loop 240. The opposite ends 238 of the metallic wire 236 are moveable to reduce the size of the loop 240. When the metallic wire 236 is disposed in a single lumen 242 or two adjacent lumen 242, as illustrated in FIG. 4, the opposite ends 238 are simply pulled through the tubular member 212 and the loop 240 is reduced in size. Accordingly the metallic wire 236 of the loop 240 slices through the lead 100. The severed portion of the lead 100 remains within the inner cavity 216 of the tubular member 212 and the apparatus is removed from the patient.

Alternatively, as illustrated in FIG. 5, in some embodiments, two separate lumens 242 are employed and the adjustment mechanism 246 is utilized. One lumen is preferably adjacent or nearly so. As described above, the lead 100 is received in the inner cavity 216 and extends outwardly at the distal end 218 and through the loop 240. The adjustment mechanism 246 is actuated by rotating the rotatable pin 248, preferably using handle 220. Accordingly, one of the opposite ends 238 is wound around the rotatable pin 248 and the size of the loop 240 is reduced. The lead 100 is captured between the insert 244 and the loop 240. The cutting surface 232 of the insert 244 and the metallic wire 236 of the loop 240 slice through the lead 100. The severed portion of the lead 100 remains within the inner cavity 216 of the tubular member 212 and the apparatus 10 is removed from the patient.

Figure 6A:
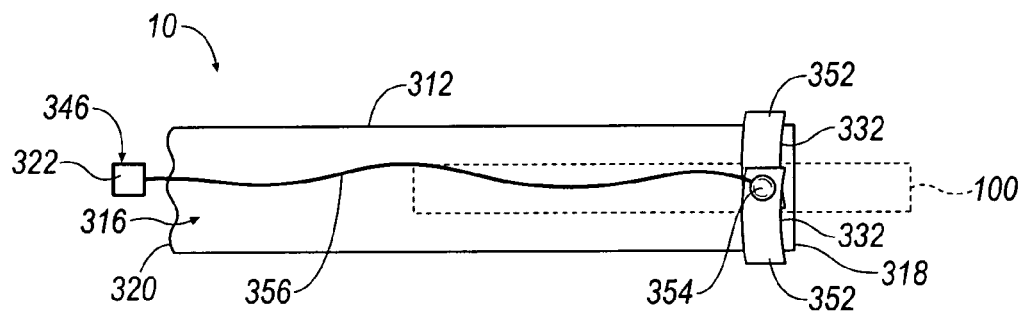
FIGS. 6A-6C illustrate a perspective view of an endocardial lead removing apparatus of another embodiment of the present invention.
Figure 6B:
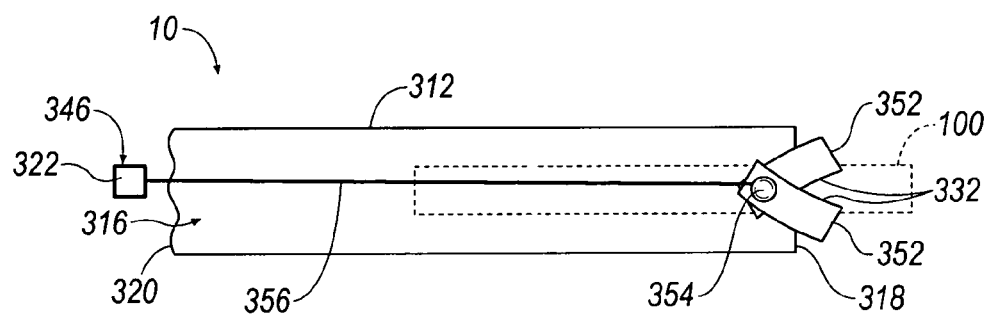
Figure 6C:
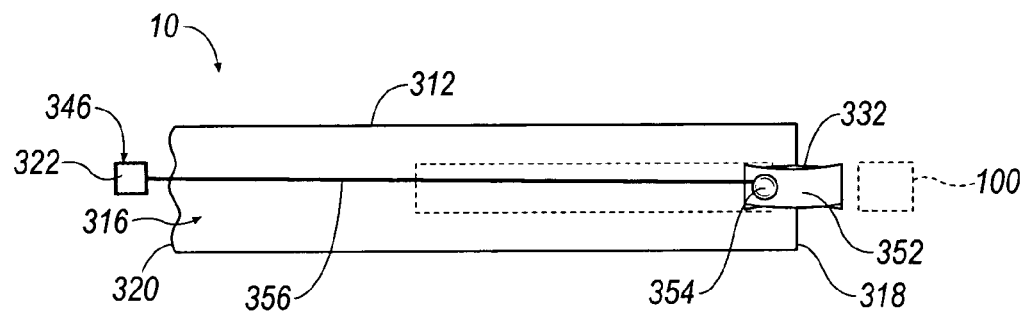
Figure 7:
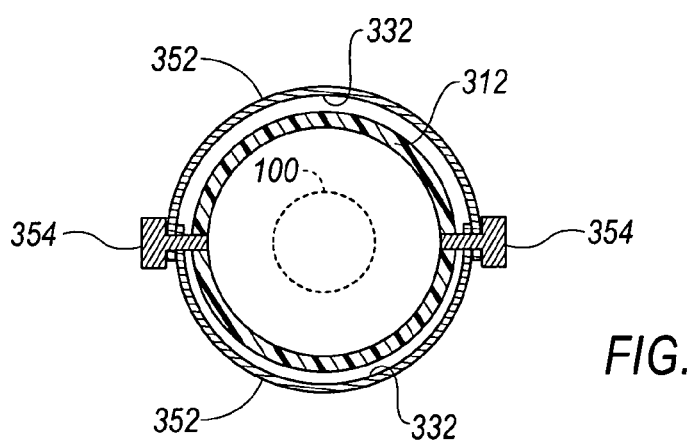
FIG. 7 illustrates an end view of the endocardial lead removing apparatus of one embodiment, without limitation.

Now referring to FIGS. 6-8, another embodiment of the apparatus 10 of the present invention is illustrated. Again the apparatus 10 includes a tubular member 312 having a distal end 318 and a proximal end 320. The tubular member 312 is preferably a metal coil shaft to allow for flexibility while resisting compression during operations. However, any material is contemplated by the present invention.

At least one blade 352 is pivotally connected to the distal end 318 of the tubular member 312. As seen in FIGS. 6A-6C, two blades 352 are pivotally connected at the distal end 318 by a pivot pin 354. Each of the blades 352 is generally arcuate to define a cutting surface 332. Further, the blades 352 are moveable between a retracted position (FIG. 6A) and an extended position (FIGS. 6B-6C).

Figure 8A:
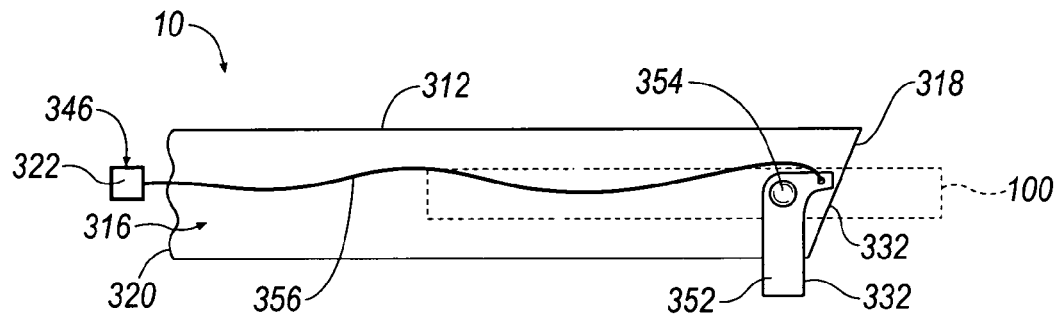
FIGS. 8A-8C illustrate a perspective view of an alternate embodiment of the endocardial lead removing apparatus of an embodiment having only one blade.
Figure 8B:
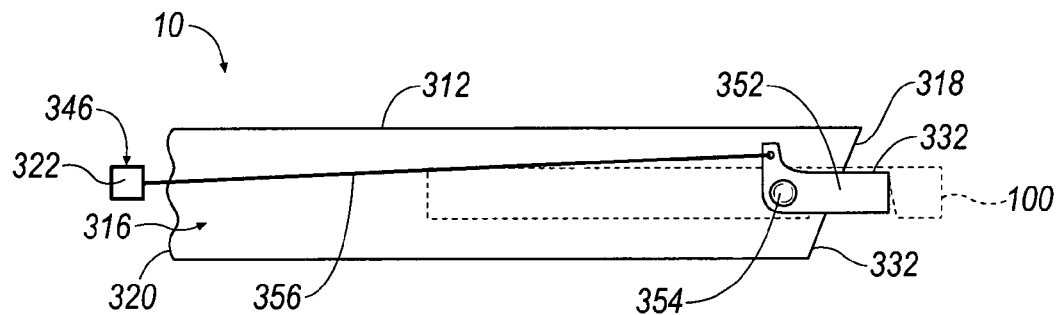
Figure 8C:
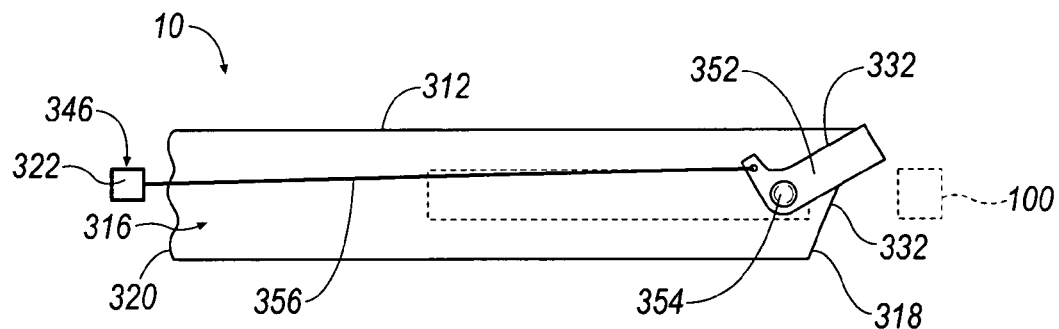

As an alternate configuration, seen in FIGS. 8A-8C, the apparatus 10 includes only one blade 352. Again, the blade 352 is pivotally connected at the distal end 318 by the pivot pin 354. The blade 352 is generally arcuate to define an inner cutting surface 332. The distal end 318 of the tubular member 312 is generally angled and defines a second cutting surface 332. The blade 352 is moveable between the retracted position (FIG. 8A) and the extended position (FIGS. 8B-8C).

The apparatus 10 of another embodiment further includes an adjustment mechanism 346. The adjustment mechanism 246 pivots the blade(s) 352 between the retracted and extended positions. By way of example, the adjustment mechanism 346 may include an outer sheath (not shown) that receives the tubular member 312 and is moveable longitudinally along the tubular member 312. A distal end of the outer sheath generally aligns with the distal end 318 of the tubular member 312 and engages the blade(s) 352. Continued longitudinal movement of the outer sheath urges the blades(s) 352 about the pivot pin 354 to pivot from the retracted to the extended position.

As a further example and illustrated in FIGS. 6 and 8, the adjustment mechanism 346 includes a pull wire 356. The pull wire 356 is attached to the blade(s) 352 and extends within an inner cavity 316 of the tubular member 312. A proximal end of the pull wire 356 is preferably joined to a handle 322.

In operation, the embodiment of apparatus 10 of FIGS. 6-8 is inserted within a patient's heart or other anatomical part containing a lead and receives the lead 100 within the inner cavity 316 of the tubular member 312. Once the distal end 318 of the apparatus 10 is positioned as near as possible to the embedded electrode tip within the patient's body the adjustment mechanism 346 is actuated. As shown, tension is applied to the pull wire 356, preferably at the handle 322, and the blade(s) 352 pivot about the pivot pin 354. The lead 100 is captured between the cutting surfaces 332 of the two blades 352 (FIGS. 6A-6C). Alternately, the lead 100 is captured between the cutting surface 332 of the one blade 352 and the cutting surface 332 of the distal end 318 of the tubular member 312 (FIGS. 8A-8C). Additional tension is applied to the pull wire 356 and the cutting surfaces 332 cut through the lead 100. The severed portion of the lead 100 remains within the inner cavity 316 of the tubular member 312 and the apparatus 10 is removed from the patient's body.

Figure 9:
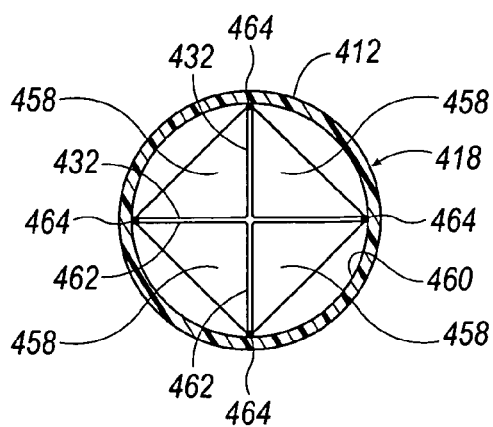
FIG. 9 illustrates a perspective view of an endocardial lead removing apparatus of another embodiment of the present invention.

Referring to FIGS. 9-10, another embodiment of the apparatus 10 of the present invention is illustrated. The apparatus 10 includes a tubular member 412 having a distal end 418 and a proximal end 420. The tubular member 412 defines a longitudinal axis A-A and an inner cavity 416. The tubular member 412 is generally flexible and is preferably made from a plastic or polymer material. However, any material is contemplated by the present invention.

At least one tooth 458 is generally positioned at the distal end 418 of the tubular member 412 within the inner cavity 416. The tubular member 412 includes a tubular wall 460 defining the inner cavity 416. The tooth 458 connects to the tubular wall 460. The at least one tooth 458 includes a plurality of edges 462 and at least one of the edges 462 is a cutting surface 432. As illustrated, this embodiment of the apparatus 10 comprises four teeth 458. However, the present invention contemplates a plurality of teeth 458 or even only one tooth 458. As shown the four teeth 458 of the illustrated embodiment are generally triangular; however, the present invention also contemplates asymmetrically shaped teeth 458.

Figure 10A:
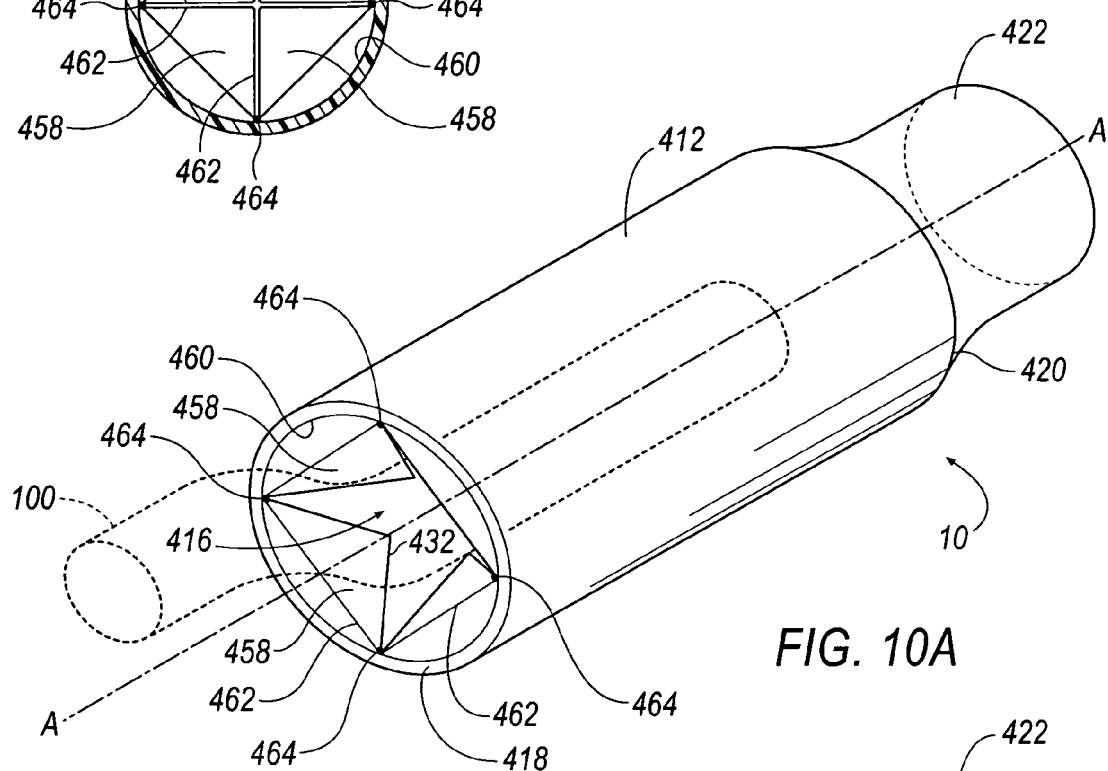
FIGS. 10A-10B illustrate a perspective end view of the endocardial lead removing apparatus of one embodiment having teeth retracted and extended, respectively.
Figure 10B:
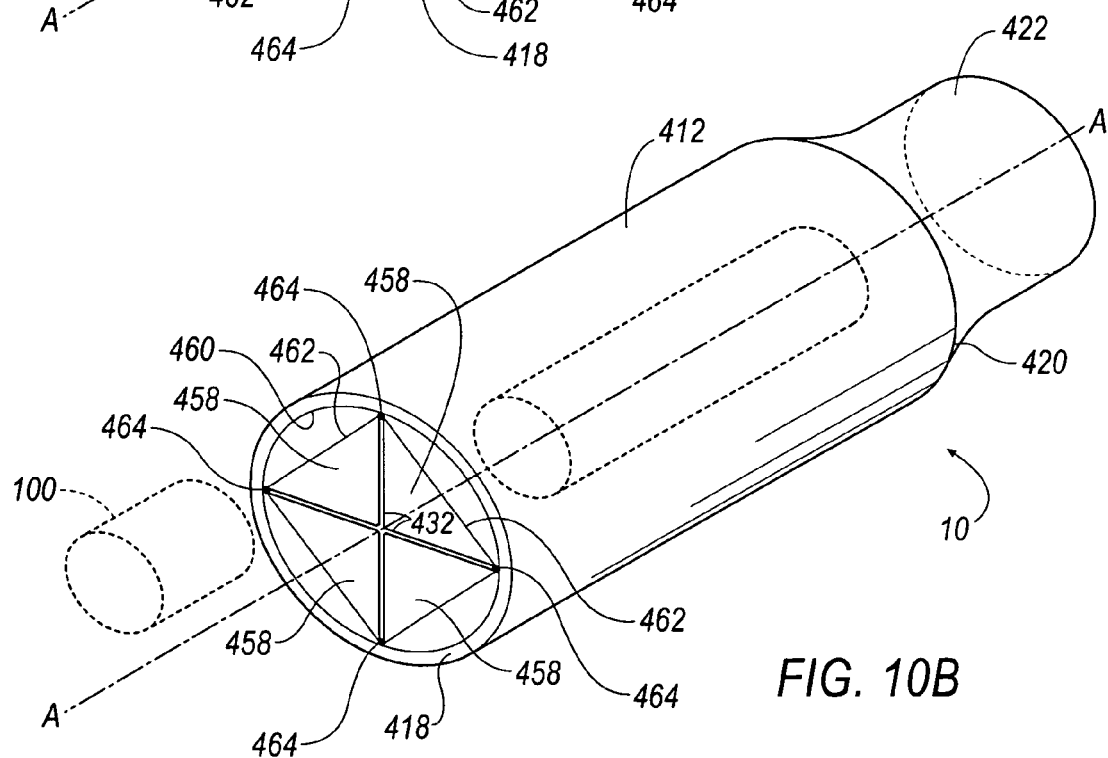

The teeth 458 of this embodiment are moveable between a retracted position and an extended position. The retracted position, as shown in FIG. 10A, positions the teeth 458 generally parallel to the tubular wall 460 of the tubular member 412. In contrast, the extended position, as shown in FIG. 10B, positions the teeth 458 generally orthogonal to the tubular wall 460 of the tubular member 412. Accordingly, when the teeth 458 are in the extended position the tubular member 412 has a reduced inner diameter.

A hinge mechanism 464 connects the teeth 458 to the tubular wall 460 of the tubular member 412. The hinge mechanism 464 adjusts the teeth 458 between the retracted position and the extended position to place the cutting surfaces 432 of the teeth 458 in contact with the lead 100. Optionally, the apparatus 10 may include an actuator (not shown) for adjusting the teeth 458 between the positions. Otherwise, the movement of the teeth 458 between the positions is manually actuated by a handle 422 at the proximal end 420 of the tubular member 412.

In operation, this embodiment of apparatus 10 is inserted within a patient's heart or other anatomical part containing a lead and positioned near the embedded electrode tip. The free end of the lead 100 is received within the inner cavity 416 of the tubular member 412. As the tubular member 412 is extended over the lead 100, the teeth 458 are in the retracted position and generally parallel to the tubular wall 460. Once the distal end 418 of the tubular member 412 is positioned as near as possible to the embedded electrode tip, the tubular member 412 is retracted. Extension and retraction of the tubular member 412 is facilitated by the handle 422 at the proximal end 420. When the tubular member 412 is retracted, contact between the cutting surface 432 and the lead 100 urges the teeth 458 to the extended position generally orthogonal to the tubular wall 460. Accordingly, the lead 100 is captured by the teeth 458 in the reduced diameter of the tubular member. Continued extension and retraction of the tubular member 412 over the lead 100 moves the teeth 458 between the retracted and extended positions. The cutting surfaces 432 repetitively contact the lead 100 and cut through. Once severed, the cut portion of the lead 100 remains within the inner cavity 416 of the tubular member 412 and the apparatus 10 is removed from the patient.

Figure 11:
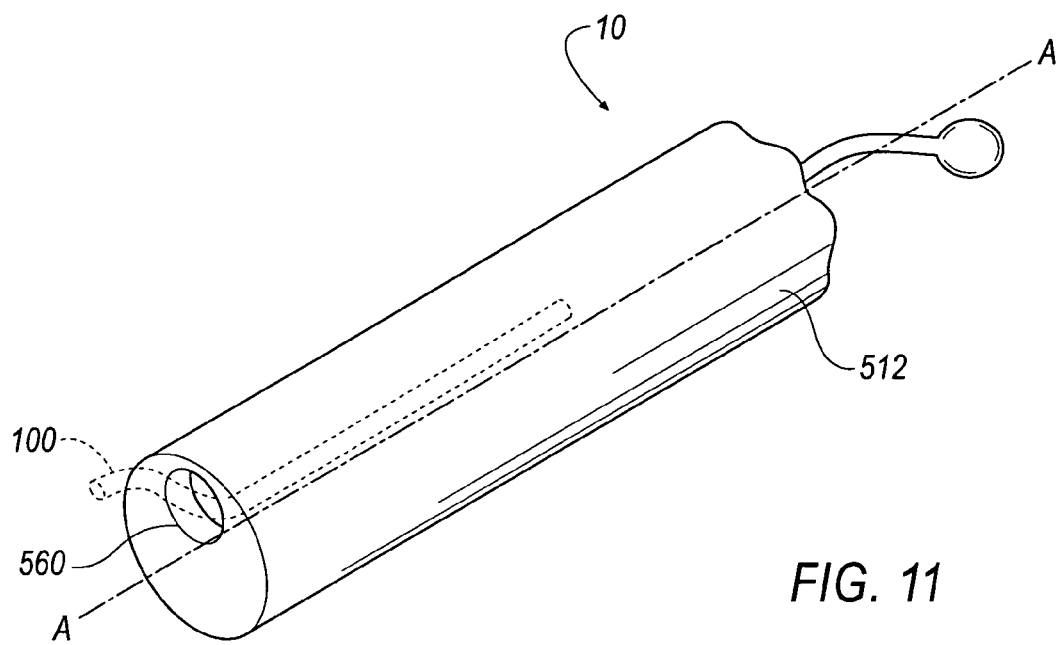
FIG. 11 illustrates a perspective view of an endocardial lead removing apparatus of a fifth embodiment of the present invention.
Figure 12:
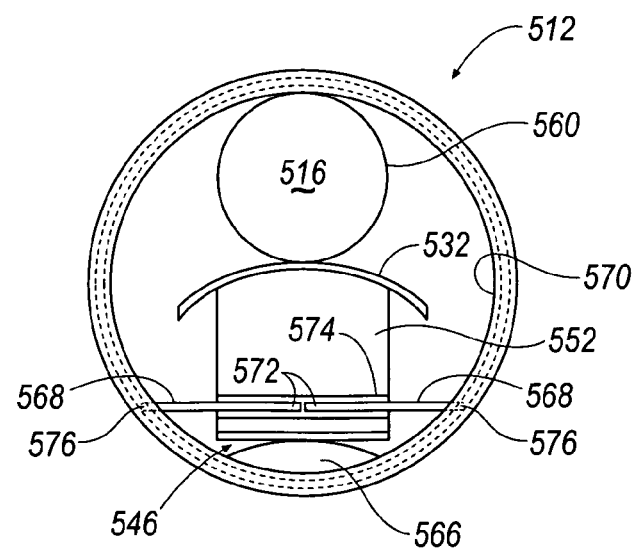
FIG. 12 illustrates a perspective end view of the endocardial lead removing apparatus of the fifth embodiment including a blade and adjustment mechanism.

Referring to FIGS. 11-12, a fifth embodiment of the apparatus 10 of the present invention is illustrated. The apparatus 10 includes a tubular member 512 defining a tubular wall 560 and a longitudinal axis A-A. The tubular member 512 is generally flexible and made from a plastic or polymer material; however, any material is contemplated by the present invention. The tubular member 512 and tubular wall 560 define an inner cavity 516. The inner cavity 516 is generally offset from the longitudinal axis A-A of the tubular member 512 in order to accommodate a blade 552 and adjustment mechanism 546 within the tubular wall 560.

The apparatus 10 includes the blade 552 disposed within the tubular wall 560 of the tubular member 512. The blade 552, by way of the adjustment mechanism 546, is moveable between a retracted position and an extended position. Further, the blade 552 includes a generally arcuate cutting surface 532.

The adjustment mechanism 546 of the fifth embodiment is pneumatically actuated. As seen in FIG. 12, the adjustment mechanism 546 includes an inflatable device 566, such as a balloon and the like. The inflatable device 566 is disposed within the tubular wall 560 and placed adjacent the blade 552 at an end opposite the cutting surface 532. Expansion and retraction of the inflatable device 566 expands or retracts the cutting surface 532 of the blade 552 into the inner cavity 516 of the tubular member.

Further, the adjustment mechanism 546 includes a guide comprising of two projecting arms 568 and a track 570. The guide facilitates movement of the blade 552 between the retracted and extended positions to insert the cutting surface 532 into the inner cavity 516. The blade 552 is adapted to receive first ends 572 of each of the projecting arms 568. As illustrated in FIG. 12, the blade includes a notch 574. Received within the notch 574 are the first ends 572 of the projecting arms 568. Accordingly, the projection arms 568 are generally parallel to the cutting surface 532 of the blade 552. The projecting arms 568 slide within the notch 574. Second ends 576 of the projecting arms 568 are received within the track 570. The track 570 is disposed within the tubular wall 560 and extends circumferentially about the tubular member 512.

In operation, the fifth embodiment of apparatus 10 of FIGS. 11-12 is inserted within a patient's heart or other anatomical part containing a lead and positioned as near as possible to the electrode tip embedded within the body. The free end of the lead 100 is received within the inner cavity 516 of the tubular member 512. Air is supplied through a catheter (not shown) to the inflatable device 566 or balloon. The inflatable device 566 expands thereby urging the blade 552 from the retracted position to the expanded position and inserting the cutting surface 532 of the blade 552 into the inner cavity 516. Further, as the blade 552 moves from the retracted position to the expanded position the second ends 576 of the projecting arms 568 move along the track 570 sliding within the notch 574 as appropriate, to accommodate the varying width of the inner cavity 516. The cutting surface 532 of the blade 552 cuts through the lead 100. Once severed, the cut portion of the lead 100 remains within the inner cavity 516 and the apparatus 10 is removed from the patient.

While the present invention has been particularly shown and described with reference to the foregoing preferred and alternative embodiments, it should be understood by those skilled in the art that various alternatives to the embodiments of the invention described herein may be employed in practicing the invention without departing from the spirit and scope of the invention as defined in the following claims. It is intended that the following claims define the scope of the invention and that the apparatus within the scope of these claims and their equivalents be covered thereby. This description of the invention should be understood to include all novel and non-obvious combinations of elements described herein, and claims may be present in this or a later application to any novel and non-obvious combination of these elements. The foregoing embodiments are illustrative, and no single feature or element is essential to all possible combination that may be claimed in this or a later application. Where the claims recite "a" or "a first" element of the equivalent thereof, such claims should be understood to include incorporation of one or more such elements, neither requiring nor excluding two or more such elements.

What is claimed is:

1. An endocardial lead removing apparatus for removing a lead implanted within a patient, said apparatus comprising:
an outer tubular member having a distal end and an outer lateral surface;
an inner tubular member received within said outer tubular member, the inner tubular member having a distal end and an outer lateral surface; and wherein each of said inner and outer tubular members defines a channel in their respective outer lateral surfaces for receiving the lead, said channel having at least one cutting surface formed in their respective outer lateral surfaces, wherein outer tubular member includes a lateral protrusion at its distal end, wherein the protrusion of the outer tubular member is part of and aligned with the outer lateral surface and is curved with the same curvature of the outer tubular member, wherein the lateral protrusion laterally protrudes relative to the cutting surface, and wherein the inner tubular member includes a lateral protrusion at its distal end, wherein the protrusion of the inner tubular member is part of and aligned with the outer lateral surface and is curved with the same curvature of the inner tubular member, wherein the lateral protrusion laterally protrudes relative to the cutting surface;

wherein the inner tubular member and the outer tubular member are open distal of the lateral protrusions;

wherein said tubular members are independently rotatable relative to each other, wherein when the protrusions of the inner tubular member and the outer tubular member are adjacent each other, a closed window is formed proximal to the protrusions such that the lead may be captured within the inner tubular member and extend out the window, with the lead being entirely bounded by portions of the tubular members defining the closed window and being positioned between the cutting surfaces, such that rotation in opposite directions cuts the lead while the lead is captured.

2. The apparatus of claim 1, wherein said channels of said inner and outer tubular members are generally L-shaped having a longitudinal opening and a lateral opening generally orthogonal to the longitudinal opening.

3. The apparatus of claim 1, wherein said channels of said inner and outer tubular members are generally T-shaped having a longitudinal opening and two lateral openings generally orthogonal to the longitudinal opening.

4. The apparatus of claim 3, wherein said lateral openings are bounded by three edges.

5. The apparatus of claim 4, wherein at least one of said three edges is said cutting surface of said channel.

6. The apparatus of claim 1, wherein said inner and outer tubular members each include a handle at a proximal end.

7. The apparatus of claim 1, wherein said channels of said inner and outer tubular members are generally disposed at a distal end of each of said members.

8. The apparatus of claim 1, wherein said inner and outer tubular members are generally metallic.

9. An endocardial lead removing apparatus for removing a lead implanted within a patient, said apparatus comprising:
an outer tubular member having a longitudinal axis;
an inner tubular member received within said outer tubular member; and
wherein each of said inner and outer tubular members includes a channel for receiving the lead, said channel having a back surface orthogonal to the longitudinal axis, a cutting surface aligned with the longitudinal axis, wherein the outer tubular member includes a lateral protrusion at its distal end that is orthogonal to the longitudinal axis such that the lateral protrusion and the cutting surface form an L-shape, and wherein the inner tubular member includes a lateral protrusion at its distal end that is orthogonal to the longitudinal axis;
wherein the inner tubular member and the outer tubular member are open distal of the lateral protrusions;

wherein said tubular members are independently movable relative to each other, wherein when the protrusions of the inner tubular member and the outer tubular member are adjacent each other, a closed window is formed proximal to the protrusions such that the lead may be captured within the inner tubular member and extend out the window, with the lead being entirely bounded by portions of the tubular members defining the closed window and being positioned between the cutting surfaces such that movement of the tubular members cuts the lead while the lead is captured.

10. An endocardial lead removing apparatus for removing a lead implanted within a patient, said apparatus comprising:
an outer tubular member having a longitudinal axis and a distal end;
an inner tubular member received within said outer tubular member; and
wherein each of said inner and outer tubular members defines a channel for receiving the lead, said channel having a straight side aligned with the longitudinal axis, a back surface adjacent to and orthogonal to the straight side, and a cutting surface aligned with the longitudinal axis, wherein the straight side extends from the distal end to the back surface, wherein the outer tubular member includes a lateral protrusion at its distal end, wherein the lateral protrusion laterally protrudes relative to the cutting surface, and wherein the inner tubular member includes a lateral protrusion at its distal end;
wherein the inner tubular member and the outer tubular member are open distal of the lateral protrusions;
wherein said tubular members are independently movable relative to each other, wherein when the protrusions of the inner tubular member and the outer tubular member are adjacent each other, a closed window is formed proximal to the protrusions such that the lead may be captured within the inner tubular member and extend out the window, with the lead being entirely bounded by portions of the tubular members defining the closed window and being positioned between the cutting surfaces such that movement of the tubular members cuts the lead while the lead is captured.

11. An endocardial lead removing apparatus for removing a lead implanted within a patient, said apparatus comprising:
an outer tubular member having a longitudinal axis and a distal end;
an inner tubular member received within said outer tubular member; and
wherein each of said inner and outer tubular members define a channel for receiving the lead, said channel having a rear side, a back surface adjacent to the rear side, and a cutting surface adjacent to the back surface and opposite of the rear side, wherein the rear side extends from the distal end to the back surface, wherein the outer tubular member includes a lateral protrusion at its distal end, wherein the lateral protrusion has a lateral side that laterally protrudes relative to the cutting surface and a far side that extends from the lateral side to the distal end, and wherein the inner tubular member includes a lateral protrusion at its distal end wherein the lateral protrusion has a lateral side that laterally protrudes relative to the cutting surface;
wherein the inner tubular member and the outer tubular member are open distal of the lateral protrusions;
wherein said tubular members are independently movable relative to each other, wherein when the protrusions of the inner tubular member and the outer tubular member are adjacent each other, a closed window is formed proximal to the protrusions such that the lead may be captured within the inner tubular member and extend out the window, with the lead being entirely bounded by portions of the tubular members defining the closed window and being positioned between the cutting surfaces such that movement of the tubular members cuts the lead while the lead is captured.

* * * * *